United States Patent [19]

Frost

[11] Patent Number: 4,880,813
[45] Date of Patent: Nov. 14, 1989

[54] METHOD OF TREATMENT FOR ALLERGIC RHINITIS

[75] Inventor: Phillip Frost, Miami Beach, Fla.

[73] Assignee: Baker Cummins Pharmaceuticals, Inc., Miami, Fla.

[21] Appl. No.: 223,081

[22] Filed: Jul. 22, 1988

[51] Int. Cl.$^4$ ............................................. A61K 31/44
[52] U.S. Cl. .................................................... 514/282
[58] Field of Search ........................................ 514/282

[56] References Cited

U.S. PATENT DOCUMENTS 4,454,142  6/1984  Tuttle .................................. 514/282

OTHER PUBLICATIONS

Austen, *Harrison's Principles of Internal Medicine* (8th ed.—McGraw Hill, New York), pp. 391–396, (1977).
Hirsch, 1984 *Conn's Current Therapy*, (W. B. Saunders Co., Philadelphia), pp. 585–589.
Douglas, *Goodman and Gilman's The Pharmacological Basis of Therepeutics*, (7th ed.—Macmillan, New York), pp. 611–613, (1985).
Casale et al., *J. Aller. Clin. Immunol.*, 73:775–781, (1984).

Primary Examiner—Leonard Schenkman
Attorney, Agent, or Firm—Kirschstein, Ottinger, Israel & Schiffmiller

[57] ABSTRACT

A method of treating patients suffering from allergic rhinitis comprises the topical administration to the nasal passages of such patients of a liquid solution containing from about 0.5 to about 10% by weight of the narcotic antagonist nalmefene or a pharmaceutically acceptable salt thereof. The solution may be administered in spray form from a squeeze bottle or from a dropper. Administration of from about 10 to about 200 microliters of the solution into each nostril may be repeated from 1 to 5 times daily.

14 Claims, No Drawings

METHOD OF TREATMENT FOR ALLERGIC RHINITIS

BACKGROUND OF THE INVENTION

1. Field of the Invention

The invention relates to methods of treating allergic rhinitis.

2. Description of the Prior Art

Allergic rhinitis is a perennial or seasonal condition characterized by a runny, itchy nose, watery, itchy eyes, congestion, postnasal drip and associated symptoms. The basic cause of this syndrome is environmental exposure to, and inhalation of, allergens.

The treatment of choice for allergic rhinitis is avoidance of the allergens. Total avoidance of certain allergens, for example tree or weed pollens or mold spores, is virtually impossible, however, and non-specific drug treatment of allergic rhinitis is often utilized.

The most widely used agents for the treatment of allergic rhinitis are antihistamines of the $H_1$-receptor antagonist type. These agents provide some symptomatic relief of nasal and ocular itching, sneezing, rhinorrhea and excess lacrimation, but are not particularly effective in relieving congestion or postnasal drip, and many antihistamines suffer from drawbacks such as short duration of activity and side effects including drowsiness. Moreover, for maximal effectiveness, the antihistamines must be taken regularly and prophylactically.

Vasoconstricting agents are often administered alone or in conjunction with antihistamines to act as decongestants in the treatment of allergic rhinitis. Numerous untoward side effects have been associated with persistent use of such decongestants, and these drugs may act synergistically with antihistamines to produce further side effects not evident where each class of agents is administered alone. Vasoconstricting agents administered topically to the nasal passages in the form of nosedrops or spray do act to temporarily relieve nasal stuffiness, but often lead to "rebound" congestion and rhinitis medicamentosa after uncontrolled usage.

Another pharmaceutical agent that has been administered topically in the nose for treatment of allergic rhinitis is cromolyn sodium. The topical application of cromolyn sodium is moderately effective, particularly on a prophylactic basis, but burning and stinging of the nasal lining has been reported when cromolyn is used during an acute phase of rhinitis.

Corticosteroids have been administered orally, parenterally and topically for the treatment of allergic rhinitis, and often achieve dramatic effects. However, the well-known side effects of this group of drugs prevents use of the corticosteroids on a long-term basis except in very severe cases. Nasal sprays containing corticosteroids have also been utilized but may also cause systemic side effects due to absorption through the nasal mucosa.

SUMMARY OF THE INVENTION

It is the object of the present invention to provide a method of treatment for allergic rhinitis which avoids the aforementioned drawbacks of the prior art treatment methods. In keeping with this object and others that will become apparent hereinafter, the present invention resides in the topical administration to the nasal passages of a patient suffering from allergic rhinitis, the narcotic antagonist nalmefene in a pharmaceutically acceptable liquid vehicle, e.g. as a nasal spray or as nose drops.

DETAILED DESCRIPTION OF THE INVENTION

Nalmefene (6-methylene-6-desoxy-N-cyclopropylmethyl-14-dihydronormorphine) is a long-acting, potent narcotic antagonist with pure antagonist activity. Apart from its utility in antagonizing the sedation, respiratory depression and other actions of opioid agents, nalmefene has also been found useful in treating diverse conditions such as hyperkinesia in children (U.S. Pat. No. 4,454,142), senile dementia, (U.S. Pat. No. 4,511,570) and sudden infant death syndrome (U.S. Pat. No. 4,639,455), among others. Nalmefene has not hitherto been disclosed, however, as having any utility in the treatment of allergic rhinitis or any related conditions.

The method of the present invention consists of the topical administration to the nasal passages of a pharmaceutically acceptable liquid solution containing from about 0.5 to about 10.0% nalmefene by weight, and preferably from about 1.0 to about 5.0% by weight. The liquid solution can be any conventional, pharmaceutically acceptable liquid vehicle utilized for intranasal medications, for example a vehicle comprising purified water, dextrose and/or sodium chloride, polyvinylpyrrolidone and a preservative such as benzalkonium chloride.

The nalmefene-containing liquid solution can be administered to the nasal passages in the form of a nasal spray or in the form of nose drops administered from a dropper. From about 10 to about 200 microliters of the solution may be administered into each nostril from 1 to 5 times daily as required for the treatment and symptomatic relief of allergic rhinitis.

It is believed that the remarkable effectiveness of topically applied nalmefene in treating allergic rhinitis may be due to the effect of the antagonist in inhibiting mast cell degranulation provoked by endogenous opioids acting on receptors in the nasal mucosa and the upper respiratory tract. Although there have been suggestions in the medical literature that endogenous opioids might stimulate mast cell degranulation (*Journal of Allergy and Clinical Immunology*, 73(6), pp. 775-81, June 1984), there has been no prior disclosure of any narcotic antagonist being effective upon topical application to the nasal passages in directly inhibiting mast cell degranulation and the resultant symptoms of allergic rhinitis.

Solutions of nalmefene in pharmaceutically acceptable and chemically compatible liquid vehicles may be introduced according to the present invention into standard squeeze bottles with nebulizer tips, e.g., a 10 ml, 15 ml or 30 ml bottle. Alternatively, the nalmefene solution may be placed in a standard dark glass bottle stoppered with a dropper-cap arrangement. In either case, the nalmefene solution is administered directly into the nasal passages by inserting the tip of the nebulizer or the tip of the dropper into each nostril in turn and squeezing the squeeze bottle or dropper bulb to cause the solution to saturate the nasal passages.

A standard dosage amount per administration is from about 10 to about 200 microliters, and the administration of that dosage may be repeated from 1 to 5 times daily, as required. The invention is not limited, however, to any particular dosage amount per administration or per day; the invention comprehends the intranasal administration of nalmefene in a liquid vehicle for the treatment of allergic rhinitis in any dosage amount and through any specific modality, whether or not expressly discussed herein.

The method of the present invention for treating allergic rhinitis may be practiced prophylactically or on an acute or chronic basis for the treatment of the active disease. Nalmefene has few known side effects, and none which are serious enough to preclude long term use in most individuals, which is not the case with intranasally administered corticosteroids or even cromolyn sodium.

The active ingredient in the liquid solutions utilized in the methods of the present invention may be nalmefene or pharmaceutically acceptable salts thereof, such as nalmefene hydrochloride.

The following examples provide detailed illustrations of the method of the present invention and of compositions suitable for use in practicing said method. These examples are not intended, to limit or restrict the scope of the invention in any way, and should not be construed as providing durations, dosage regimens or methods of administration which must be utilized exclusively to practice the present invention.

EXAMPLES 1-5

Liquid Solutions of Nalmefene Hydrochloride for Intranasal Administration

Solutions of nalmefene hydrochloride varying in concentration from 0.5 to 10.0% (weight/weight) are prepared by dissolving in purified water (q.s. ad 10 ml) the following ingredients:

| Ingredients (in 10 ml solution) | Ex. 1 (0.5%) | Ex. 2 (1.0%) | Ex. 3 (2.0%) | Ex. 4 (5.0%) | Ex. 5 (10.0%) |
| --- | --- | --- | --- | --- | --- |
| Nalmefene HCl | 50 mg | 100 mg | 200 mg | 500 mg | 1 g |
| Polyvinyl-pyrrolidone | 100 mg | 100 mg | 100 mg | 100 mg | 100 mg |
| Benzalkonium Chloride | 2 mg | 2 mg | 2 mg | 2 mg | 2 mg |
| Dextrose | 522 mg | 481 mg | 400 mg | 156 mg | — |
| (Alternatively, substitute for Dextrose:) | | | | | |
| Sodium Chloride | 83.5 mg | 77 mg | 64 mg | 25 mg | — |

EXAMPLE 6

Method of Treatment for Allergic Rhinitis

The solution produced according to ay of Examples 1-5 is placed in a 10 ml squeeze bottle with an elongated nebulizer tip suitable for insertion into the nostril and administration of approximately 50 microliters of solution per squeeze. The nebulizer tip is then inserted and the bottle squeezed one time into each nostril of a patient suffering from allergic rhinitis. Alternatively, the solution prepared according to any of Examples 1 through 5 is placed in a dark-colored 10 ml glass bottle stoppered with a dropper-cap arrangement. The bulb of the eye dropper is squeezed and then released to draw solution from the bottle into the dropper, and one drop (approximately 50 microliters) of solution is inserted into each nostril of the patient suffering from allergic rhinitis. Whether the spray bottle or dropper is used, the treatment may be repeated from 1 to 5 times daily as required.

The methods of the present invention are suitable for treating both the seasonal and perennial varieties of allergic rhinitis without causing any of the usual side effects that are the hallmarks of prior art treatment agents such as antihistamines, vasoconstricting decongestants, or corticosteroids. Moreover, the liquid solutions of nalmefene or its pharmaceutically acceptable salts utilized in the present invention are less likely to cause local irritation and sensitization than solutions or powders containing cromolyn sodium.

It has thus been shown that there are provided methods which achieve the various objects of the invention and which are well adapted to meet the conditions of practical use.

As various possible embodiments might be made of the above intention, and as various changes might be made in the embodiments set forth above, it is to be understood that all matters herein described are to be interpreted as illustrative and not in a limiting sense.

What is claimed as new and desired to be protected by Letters Patent is set forth in the following claims.

I claim:

1. A method of treating a patient suffering from allergic rhinitis comprising the topical administration to the nasal passages of the patient of a pharmaceutically acceptable liquid solution containing from about 0.5 to about 10.0% by weight of nalmefene or a pharmaceutically acceptable salt thereof.

2. A method according to claim 1 wherein said solution contains from about 1.0 to about 5.0% nalmefene or a pharmaceutically acceptable salt thereof by weight.

3. A method according to claim 1 wherein said solution is administered topically to the nasal passages of the patient from a spray bottle.

4. A method according to claim 1 wherein said solution is administered topically to the nasal passages of the patient from a dropper.

5. A method according to claim 1 wherein a dosage amount of from about 10 to about 200 microliters of the solution is administered into each nostril of the patient.

6. A method according to claim 5 wherein said dosage amount is administered into each nostril of the patient from 1 to 5 times daily.

7. A method according to claim 1 wherein said solution contains nalmefene hydrochloride.

8. A method according to claim 1 wherein said allergic rhinitis is seasonal in nature.

9. A method according to claim 1 wherein said allergic rhinitis is perennial in nature.

10. A method according to claim 5 wherein said dosage amount is 50 microliters of solution per nostril.

11. A method accding to claim 1 wherein said solution is a saline solution.

12. A method according to claim 1 wherein said solution contains dextrose.

13. A method according to claim 1 wherein said solution is administered to treat the active symptoms of allergic rhinitis.

14. A method of treating a patient prone to allergic rhinitis comprising the topical prophylactic administration to the nasal passages of the patient of a pharmaceutically acceptable liquid solution containing from about 0.5 to about 10.0% by weight of nalmefene or a pharmaceutically acceptable salt thereof to prevent the onset of the symptoms of allergic rhinitis.

* * * * *